United States Patent [19]

Masters et al.

[11] Patent Number: 4,794,788

[45] Date of Patent: Jan. 3, 1989

[54] METHOD AND APPARATUS FOR RHEOLOGICAL TESTING

[75] Inventors: Thomas D. Masters, Woodmere; Henry A. Pawlowski, Seville, both of Ohio

[73] Assignee: Monsanto Company, St. Louis, Mo.

[21] Appl. No.: 104,611

[22] Filed: Oct. 5, 1987

[51] Int. Cl.[4] .............................................. G01N 11/00
[52] U.S. Cl. ........................................... 73/59; 73/60; 73/841
[58] Field of Search .................. 73/59, 60, 841, 846, 73/54

[56] References Cited

U.S. PATENT DOCUMENTS

| | | | |
|---|---|---|---|
| 3,256,741 | 6/1966 | Wise | 73/432 |
| 3,681,980 | 8/1972 | Decker | 73/794 |
| 4,095,461 | 6/1978 | Starita | 73/101 |
| 4,154,093 | 5/1979 | Smith et al. | 73/54 |
| 4,343,190 | 8/1982 | Danko et al. | 73/846 |
| 4,501,155 | 2/1985 | Garritano | 73/847 |
| 4,535,621 | 8/1985 | Gervais et al. | 73/59 |
| 4,546,438 | 10/1985 | Prewitt et al. | 364/473 |
| 4,552,025 | 11/1985 | Barker et al. | 73/846 |
| 4,559,812 | 12/1985 | Kitchen | 73/59 |
| 4,584,882 | 4/1986 | Tosaki | 73/847 |
| 4,601,195 | 7/1986 | Garritano | 73/60 |
| 4,602,501 | 7/1986 | Hirata | 73/54 |
| 4,667,519 | 5/1987 | Burg et al. | 73/815 |

OTHER PUBLICATIONS

D. M. Danko et al., "An Application of Mini-Computers for the Determination . . ." Test Equipment (?).

Primary Examiner—Stewart J. Levy
Assistant Examiner—Hezron E. Williams
Attorney, Agent, or Firm—Gordon B. Seward

[57] ABSTRACT

A method and apparatus for testing samples of visco-elastic materials are shown, in which the sample is subjected to a sinusoidal excitation and the response to the excitation is measured. By sampling the response at at least three data points equally spaced through a single cycle of excitation and making the proper calculations based on the data points, the storage modulus or the loss modulus of the materials, or both, can be obtained. The apparatus includes a rotary drive, eccentric, sample holder, a rotor or moving die, a torque transducer, excitation means, response measuring means, data handler and a sampler to obtain responses at predetermined intervals.

14 Claims, 2 Drawing Sheets

METHOD AND APPARATUS FOR RHEOLOGICAL TESTING

BACKGROUND OF THE INVENTION

This invention relates to methods for testing viscoelastic materials to determine their rheological properties, and to apparatus for performing such testing. More particularly, this invention relates to methods for obtaining values of the storage modulus, the loss modulus, or both, for viscoelastic materials, and to apparatus for obtaining such values.

The response of viscoelastic materials like rubber to deformation is not simple compared to that of a metal spring or a liquid. Rubber has a response somewhere between that of a metal spring and a liquid such as water. A metal spring resists deformation proportionately to the amount of deformation or strain put on the spring. It doesn't matter how slow or fast one moves the spring but only how far it is moved. A liquid such as water resists deformation proportionately to the rate of deformation or strain rate. If one stops moving in water, resistance by the water stops.

When rubber is deformed, some of its resistance to deformation is proportional to the amount of deformation and some of its resistance is proportional to the rate of deformation. The constant used for a particular rubber to describe the magnitude of that rubber's resistance to the amount of deformation is G' or S' (called G Prime or S Prime). Note that G has a scientific meaning which is the shear modulus while S is a general term referring to the "stiffness" of the rubber. A stiffer rubber will have a larger G' or S'. This constant also indicates the amount of energy which can be stored by the rubber. The constant used to describe that same rubber's resistance to the rate of deformation is G" or S" (called G double prime or S double prime). This constant also indicates the amount of energy converted to heat and lost. (The ratio of these two (G"/G' or S"/S') is an important rubber property called Tan ($\delta$)).

Prior art devices for testing viscoelastic materials are typified by curemeters or rheometers designed to measure the properties of a rubber compound as it is vulcanized. Such devices often features an oscillating rotor placed in a sample confined under pressure, wherein the rotor is driven by an eccentric mechanism to excite the rubber sample in a sinusoidal pattern and the applied torque is measured. Other devices of this sort eliminate the rotor, and drive one of the confining dies, measuring resultant torque on the opposite die. Typically, values for torque at maximum displacement are obtained, and are assumed to represent the storage modulus of the material; the torque at zero deformation is representative of the loss modulus. Alternatively, after determining torque at maximum displacement, the maximum torque value is also measured, and the value of the loss modulus is calculated by using the pythagorean theorum (assumed to be equal to the square root of the sum of the maximum torque value squared less the square of the value of the torque at maximum displacement). The nature of these calculations is such that errors are "built into" them. A need exists for greater accuracy in calculating the modulus components of viscoelastic materials, so that their behavior is better characterized.

BRIEF SUMMARY OF THE INVENTION

The method of the invention provides greater accuracy for this calculation, as will be set forth. The method, briefly stated, determines a modulus of a viscoelastic material by separately measuring the response of the material and of a standard to sinusoidal excitation at at least three data points equally spaced throughout a cycle, separately applying a calculation operation such as a discrete Fourier transform to the data points so as to convert the material data points into values representative of the storage and/or loss modulus of the material and to convert the standard data points into values representing torque at a specific phase angle, and correcting the values representative of the storage and/or loss modulus of the material by reference to the torque standard torque and phase angle to obtain values indicative of the storage and/or loss modulus for the material.

The apparatus of the invention briefly described, comprises a rotary drive, with an eccentric to translate rotary motion int sinusoidal oscillating motion, a sample holder, means to apply excitation to a sample, means to measure a resultant response to the excitation, a data handler to convert the response data, and a sampling mechanism cooperating with the rotary drive to obtain a plurality of responses at predetermined intervals and a single reference point during each revolution of the rotary drive.

Preferred embodiments of the apparatus of the invention can be of the oscillating disc rheometer (ODR) type or the moving die rheometer (MDR) type. In the former, typified by the device shown in U.S. Pat. No. 3,681,980, a rotor is located in a sample-holding space, and is oscillated to provide the excitation to the sample. A torque transducer in the rotor shaft measures the resistance of the sample to the excitation. The latter (MDR) type, as exemplified in U.S. Pat. Nos. 4,343,190 and 4,552,025, features an arrangement wherein the sample is enclosed between two opposing dies; one of the dies is oscillated, and the resultant forces are measured on the other die, again typically using a torque transducer.

Preferred embodiments of the method of the invention include sampling at least four response points during a cycle of excitaion, more preferably eight to 80 points, and even more preferably sixteen points. The number of sampling points is theoretically unlimited, however, as a practical matter, the advantages of using more than sixteen points begin to be outweighed by the complexity and cost of so doing. Moreover, it has been found that the use of sixteen sampling points is an excellent compromise, giving a high degree of accuracy to the method without undue complication.

A more complete understanding of the invention can be obtained by reference to the drawings and to the description of the preferred embodiments following.

DETAILED DESCRIPTION OF THE INVENTION

Figure 1:
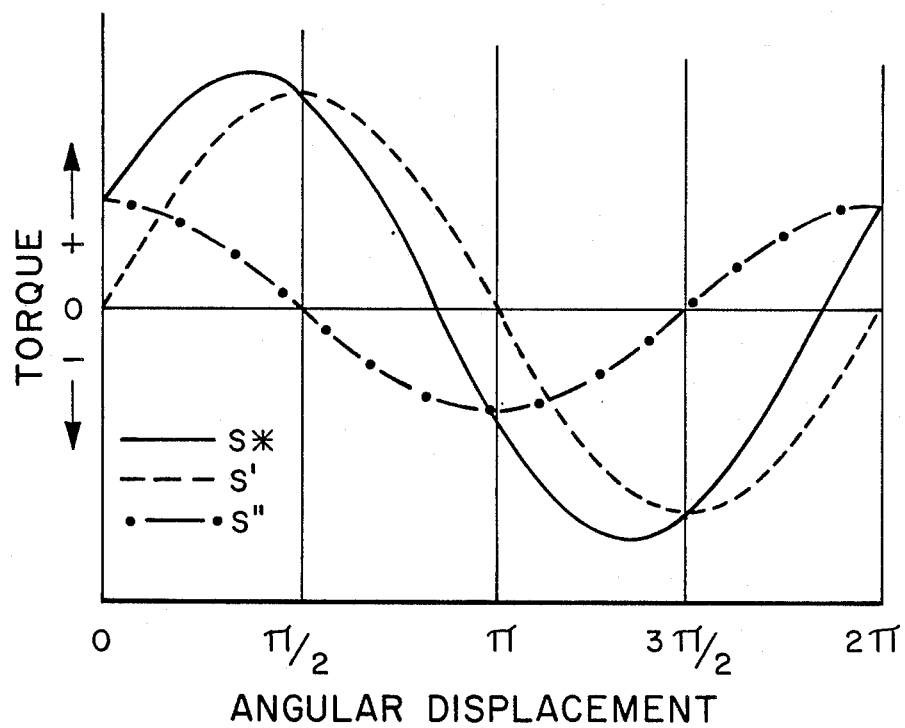
FIG. 1 is a graphic representation of the curves generated by the complex modulus (S*) and its components, the storage modulus (S') and the loss modulus (S") over a single complete cycle of excitation.

The preferred method of the invention can be mathematically described, relating the geometry of the apparatus to the relationship between the components of the modulus of the viscoelastic material under test.

The torque signal from a sinusoidally oscillating rheometer can be represented by the equation $$S_{(t)} = (S^*) \sin(wt + \delta)$$

where $S_{(t)}$ is the torque signal at time t, $S^*$ represents the complex modulus of the material, w is the oscillation frequency, t is time and $\delta$ is the phase shift from displacement due to the nature of the material. An alternate form of representing this relationship is the equation $$S_{(t)} = (S')(\sin wt) + (S'')(\cos wt)$$

where (S') is the storage component of the torque, (S'') is the loss component of the torque. This equation is developed from the relationships $$S^{*2} = S'^2 + S''^2$$

and $$\delta = \tan^{-1}(S'')/S'$$

Prior art devices output only S' during a test, since torque readings are taken only at the two positions of maximum strain. Calibration of the devices is required, with mechanical adjustments and settings performed using a metal spring torque standard.

Using the preferred method of the invention, calibration is done automatically by the data handler. The torque standard is installed as in the prior art. After warmup of the torque standard the calibration procedure is started, with the position of the zero location on the torque sampler relative to the torque standard being stored in the computer's permanent memory. Dividing the expected torque standard value by the actual measurement gives a calibration factor for the rheometer. This factor is also stored in the computer's permanent memory. The rheometer is then ready for testing the sample.

The method uses, typically, sixteen $S_{(t)}$ values, together with their locations, to determine both S' and S'' for each cycle. The locations of the sixteen $S_{(t)}$ values can be thought of as representing sixteen equidistant points on a circle. Thus, if the first point is at 0 degrees, the second point will be at 22.5 degrees, the third at 45 degrees, and so on.

The method calculates S' by multiplying each $S_{(t)}$ value by the sine of its angle location. All sixteen products are then summed and multiplied by an integration constant to give S'. S'' can be calculated in the same way by substituting the cosine in place of the sine.

Advantages of the method include an inherent increase in the "signal-to-noise" ratio, since the method samples sixteen points instead of two, and the "noise" is inversely proportional to the square root of the sum of the squares of the errors in each of the sample points.

Also, since all torque samples are taken by the same sampling detector the errors introduced by using two different sampling detectors are eliminated.

The calculations involved in the method, described as Fourier transforms, act as low-pass filters, inherently minimizing "noise."

Finally, the method permits self-diagnostics of the rheometer, since the magnitude of higher harmonic output indicates extraneous defects.

FIG. 1 shows the sinusoidal curves representing the complex modulus (S*), the storage modulus (S') and the loss modulus (S'') over a single complete cycle. The ordinate line represents torque, with a zero torque line and positive and negative torque values on either side. The abscissa represents angular displacement, $2\pi$ being a full 360° of shaft revolution.

Figure 2:
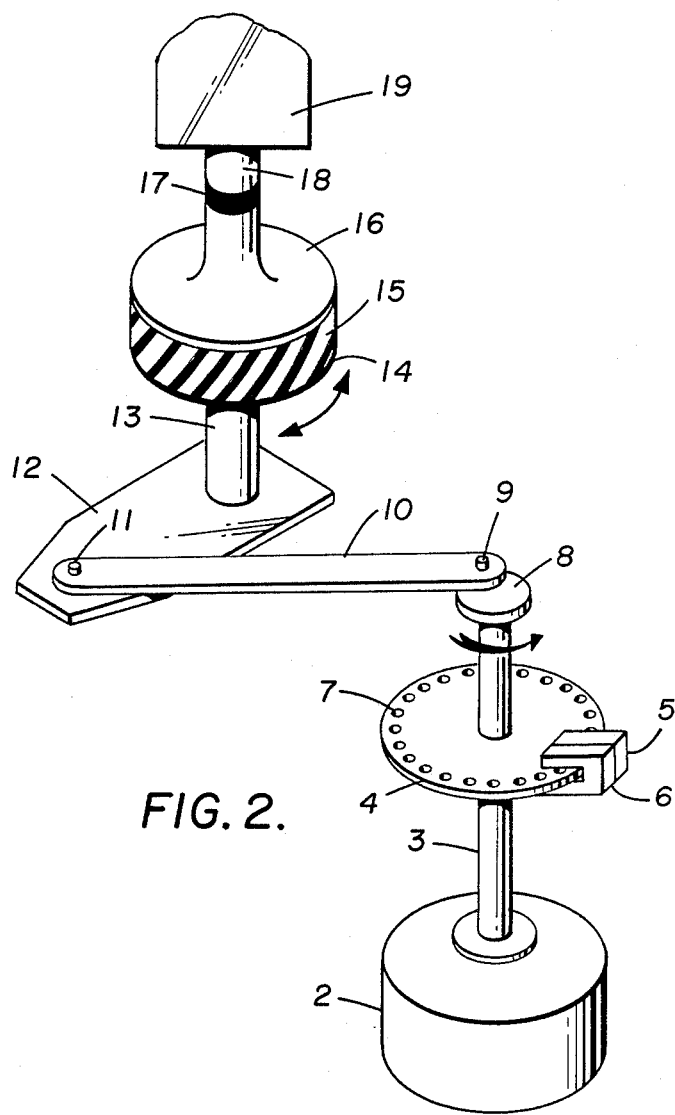
FIG. 2 is a somewhat stylized pictorial view of the pertinent portions of a rheometer.

FIG. 2 depicts an embodiment of the apparatus of the invention, showing the essential portion of a rheometer. Motor 2 drives shaft 3, on which is mounted disk 4. Disk 4 has sixteen evenly spaced holes, one of which 7 is elongated into an elipse. Mounted around the edge of disk 4 are sample LED photodiode 5 and reference LED photodiode 6. The other end of shaft 3 is connected to mounting 8 which contains eccentric pin 9. Eccentric arm 10 is positioned on eccentric pin 9 on one end and another eccentric pin 11 on the other end. Eccentric pin 11 is fixed to drive plate 12 on which is mounted shaft 13 which supports lower die 14. A sample 15 of viscoelastic material to be tested is contained between lower die 14 and upper die 16, which in turn is fixed through torque transducer 17 to upper shaft 18, which is fastened to upper support 19.

Motor 2 rotates shaft 3 at a set speed, causing disk 4 to rotate. LED-photodiodes 5 and 6 record the holes in disk 4 as they pass, sending sampling and calibrating pulses to the data handling and controlling device (not shown). Since the rotation of shaft 3 also actuates an oscillating rotation of lower die 14 through the eccentric linkage, the sampling and calibrating pulses also indicate the relative position of lower die 14 in its oscillatory cycle. The torque signals generated by torque transducer 17 are also fed to the data handling and controlling device, which picks sixteen torque values in each position. The data handling and controlling device then performs the Fourier transform for each data point and generates the values of the storage and loss modulus.

Of course, the rheometer can also include heating and temperature controlling mechanisms (not shown) to provide a controlled atmosphere. The sample can be enclosed under pressure during the test, as well.

While the apparatus depicted in FIG. 2 shows a moving-die rheometer (MDR), the apparatus may be in the configuration of an oscillating disk rheometer (ODR), wherein a rotor embedded in the smple is driven, and the torque measured on the rotor drive shaft.

In another modification of the apparatus, the sampling is performed by means of a pulse encoder mounted on the motor shaft (instead of the disk with its LED-photodiodes). The pulse encoder produces a pulse at evenly spaced angular intervals and an additional reference pulse once per revolution. Typically, a pulse encoder is used which produces 2000 pulses per revolution. This pulse signal is then divided by a constant (typically 25–125) and the data handling system samples the torque at this lower rate (16–80 samples per cycle). The zero reference pulse is used to signal the beginning of a cycle.

Although the invention has been illustrated by typical examples and preferred embodiments it is not limited thereto. Changes and modifications of these examples and embodiments herein chosen for purposes of disclosure can be made which do not constitute departure from the spirit and scope of the invention.

The embodiments of the invention in which an exclusive property or privilege is claimed are defined as follows:

1. The method of testing a viscoelastic material comprising the steps of (A) separately subjecting both a sample of the material and a standard to sinusoidal excitation,
(B) separately measuring a material response and a standard response at at least three displacement data points equally spaced throughout a cycle of excitation,
(C) separately applying a calculation operation to the data points to
   (i) convert the material data points into values representing either a storage modulus or a loss modulus of the material; and to (ii) convert the standard data points into values representing a standard torque and a standard phase angle, and
(D) correcting the values representing the storage modulus or loss modulus for the material.

2. The method of claim 1, wherein response is measured at at least four equally spaced points and the calculation operation is a discrete Fourier transform.

3. The method of claim 2, wherein response is measured at 8–80 equally spaced points.

4. The method of claim 3, wherein response is measured at 16 equally spaced points.

5. The method of claim 1, wherein the standard is a torsion spring.

6. The method of claim 1, and the additional step of computing the magnitude of any higher harmonics which may be obtained.

7. In a rheometer comprising, in combination,
a rotary drive adapted to produce rotary motion, an eccentric to translate rotary motion to sinusoidal, oscillating motion, sample holding means, means attached to the eccentric and adapted to apply excitation to a sample in the sample holding means, means to measure a resultant response to the excitation and means to manipulate the response data, the improvement comprising data sampling means attached to the rotary drive adapted both to sample a plurality of responses at predetermined intervals, and to signal a single reference response through each revolution of said rotary drive.

8. The rheometer of claim 7, wherein the means to apply excitation is a rotor and the means to measure response is a torque transducer on said rotor.

9. The rheometer of claim 8, wherein the sample holding means is adapted to hold the sample under pressure.

10. The rheometer of claim 7, wherein the means to apply excitation is a portion of the sample holding means.

11. The rheometer of claim 10, wherein the means to measure response is another portion of the sample holding means.

12. The rheometer of claim 7, wherein the sampling means comprises a disk containing spaced holes, cooperating with at least one LED-photodiode.

13. The rheometer of claim 12 wherein the disk contains sixteen equally-spaced holes and a reference hole, and two LED-photodiodes are present.

14. The rheometer of claim 7 wherein the sampling means comprises a pulse encoder.

* * * * *